(12) United States Patent
Isogai

(10) Patent No.: US 6,755,528 B2
(45) Date of Patent: Jun. 29, 2004

(54) SHAPE MEASUREMENT APPARATUS (75) Inventor: Naoki Isogai, Nishio (JP)

(73) Assignee: Nidek Co., Ltd., Gamagori (JP)

(*) Notice: Subject to any disclaimer, the term of this patent is extended or adjusted under 35 U.S.C. 154(b) by 0 days.

(21) Appl. No.: 10/310,761

(22) Filed: Dec. 6, 2002

(65) Prior Publication Data
US 2003/0107708 A1 Jun. 12, 2003

(30) Foreign Application Priority Data
Dec. 7, 2001 (JP) .................................. 2001-373744

(51) Int. Cl.[7] .............................................. A61B 3/10
(52) U.S. Cl. ...................................................... 351/212
(58) Field of Search ................................. 351/211, 212, 351/221; 356/124, 127; 606/4, 5

(56) References Cited

U.S. PATENT DOCUMENTS

| | | |
|---|---|---|
| 4,051,483 A | 9/1977 | Suzuki |
| 4,420,228 A | 12/1983 | Humphrey |
| 4,572,628 A | 2/1986 | Nohda |
| 5,463,430 A | 10/1995 | Isogai et al. |
| 5,532,772 A | 7/1996 | Fujieda et al. |
| 5,742,381 A | 4/1998 | Ueno |
| 5,907,388 A | 5/1999 | Fujieda |
| 6,222,621 B1 * | 4/2001 | Taguchi ..................... 356/124 |

FOREIGN PATENT DOCUMENTS

| | | |
|---|---|---|
| EP | 0 549 516 A2 | 6/1993 |
| GB | 2 177 813 A | 1/1987 |
| JP | B2 1-19896 | 4/1989 |

* cited by examiner

Primary Examiner—George Manuel
(74) Attorney, Agent, or Firm—Oliff & Berridge, PLC (57) ABSTRACT A shape measurement apparatus capable of saving time and effort of an examiner and improving measurement accuracy. The apparatus for measuring a spherical shape of an object to be examined comprising a measurement unit where a first projection optical system projects first targets for measurement onto a spherical surface to be measured, a first detection optical system detects images of the projected first targets and a calculation unit obtains a shape of the surface based on the detected images, an output unit which outputs the obtained shape, a mode setting unit which sets any one of a first measurement mode for a convex shape and a second measurement mode for a concave shape, and a condition setting unit which sets at least one of a measurement condition and an output condition based on a mode setting result, the conditions being different between the first and second measurement modes.

12 Claims, 7 Drawing Sheets

( Convex Surface )  ( Concave Surface )

SHAPE MEASUREMENT APPARATUS

BACKGROUND OF THE INVENTION

1. Field of the Invention

The present invention relates to a shape measurement apparatus for measuring a spherical shape of an object to be examined, particularly, a shape measurement apparatus suitable for measuring a spherical shape of a cornea of an eye to be examined, a spherical shape of a contact lens and the like.

2. Description of Related Art

A corneal shape measurement apparatus for measuring a spherical shape of a cornea of an eye to be examined (meridional radius of curvatures of a steepest meridian and a flattest meridian, and an axial angle in the direction of the steepest or flattest meridian) is used for measuring a spherical shape (a base curve) of a contact lens (radius of curvatures on a concave surface side) in addition to the corneal shape measurement. In this case, a convex surface is measured at the time of the measurement of the corneal shape, while a concave surface is measured at the time of that of the base curve of the contact lens. In order to comply with both of the measurements, a measurement target symmetrical to the measurement optical axis (a target which has an annular shape having the measurement optical axis at its center or four targets which are vertically and horizontally symmetrical to the measurement optical axis) is generally used.

However, the conventional apparatus does not determine whether the measured spherical surface of the object is convex or concave. Therefore, an examiner need manage measurement data and it is bothersome for the examiner. For example, as is different from the measurement of the corneal shape having a convex surface, in the case of that of the base curve of the contact lens having a concave surface, the examiner makes a memo in printed data that the data is as to the contact lens (the concave surface measurement data). In addition, in the case of the measurement of a base curve of a contact lens having an astigmatic axis depending on a corneal shape of an examinee, the direction of its principal meridian (AXIS: an axial angle) need be reversed laterally, and the examiner performs reverse by manual calculation.

Further, in the case of the measurement of the base curve of the contact lens, as is different from that of the corneal shape, a back-surface reflection (a reflection from a convex surface side at the time of the concave surface shape measurement) exists, and it results in a problem of influencing on measurement accuracy.

SUMMARY OF THE INVENTION

An object of the invention is to overcome the problems described above and to provide a shape measurement apparatus which is capable of saving time and effort of an examiner and improving measurement accuracy.

To achieve the objects and in accordance with the purpose of the present invention, a shape measurement apparatus for measuring a spherical shape of an object to be examined comprises a measurement unit where a first projection optical system projects first targets for measurement onto a spherical surface to be measured of an object to be examined, a first detection optical system detects images of the projected first targets and a calculation unit obtains a shape of the spherical surface based on the detected images of the first targets, an output unit which outputs the obtained shape of the spherical surface, a mode setting unit which sets any one of a first measurement mode for measuring a convex shape and a second measurement mode for measuring a concave shape and a condition setting unit which sets at least one of a measurement condition and an output condition based on a mode setting result, the measurement condition and the output condition in the first measurement mode being different from the measurement condition and the output condition in the second measurement mode.

In another embodiment of the present invention, a shape measurement apparatus for measuring a spherical shape of an object to be examined comprises a measurement unit where a first projection optical system projects first targets for measurement onto a spherical surface to be measured of an object to be examined, a first detection optical system detects images of the projected first targets and a calculation unit obtains a shape of the spherical surface based on the detected images of the first targets, a second projection optical system which projects second targets of a configuration or shape pattern not symmetric about a point with respect to a measurement reference axis onto the spherical surface, a second detection optical system which detects images of the projected second targets, and a judging unit which judges whether the spherical surface is a convex shape or a concave shape based on a pattern of the detected images of the second targets.

Additional objects and advantages of the invention are set forth in the description which follows, are obvious from the description, or may be learned by practicing the invention. The objects and advantages of the invention may be realized and attained by the apparatus for determining corneal ablation data and the corneal surgery apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
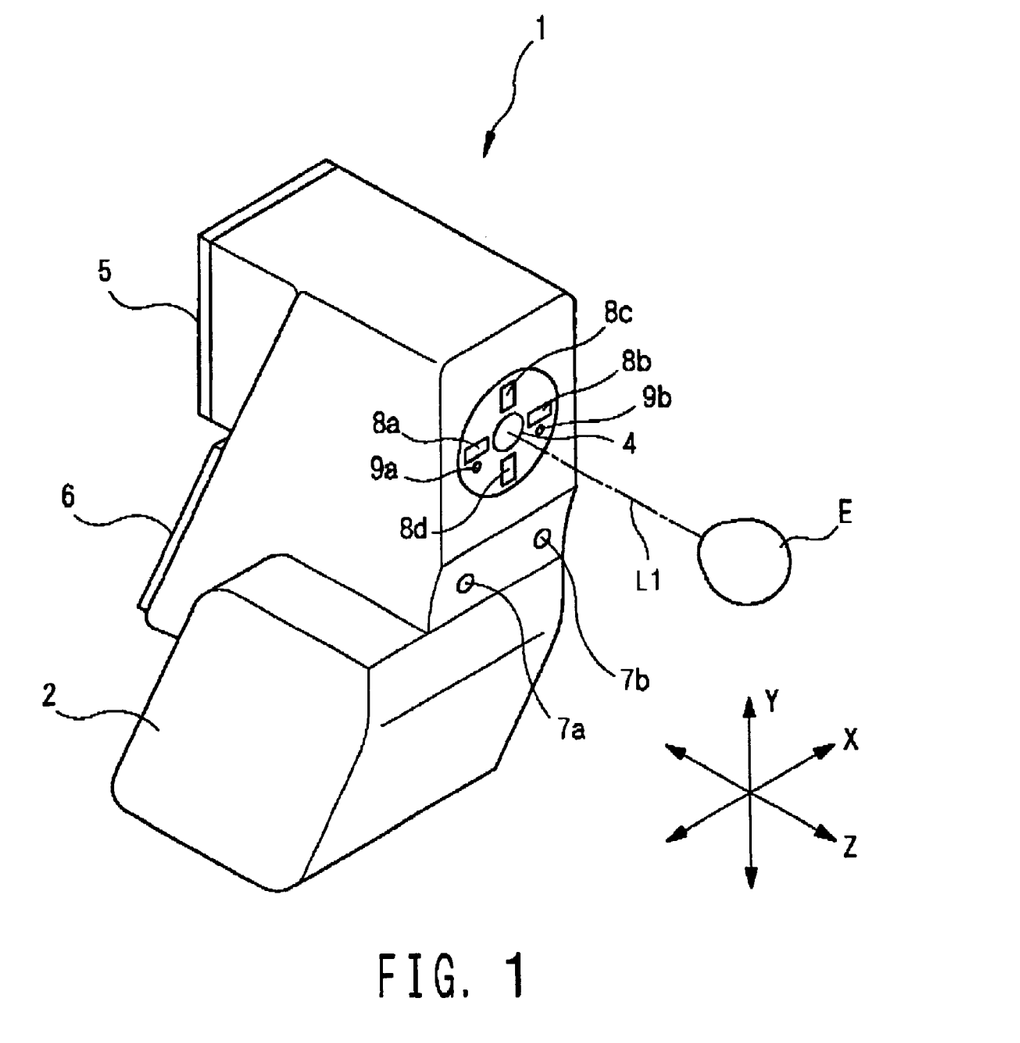
FIG. 1 is an external view schematically showing an ophthalmic apparatus consistent with the present invention.
Figure 2:
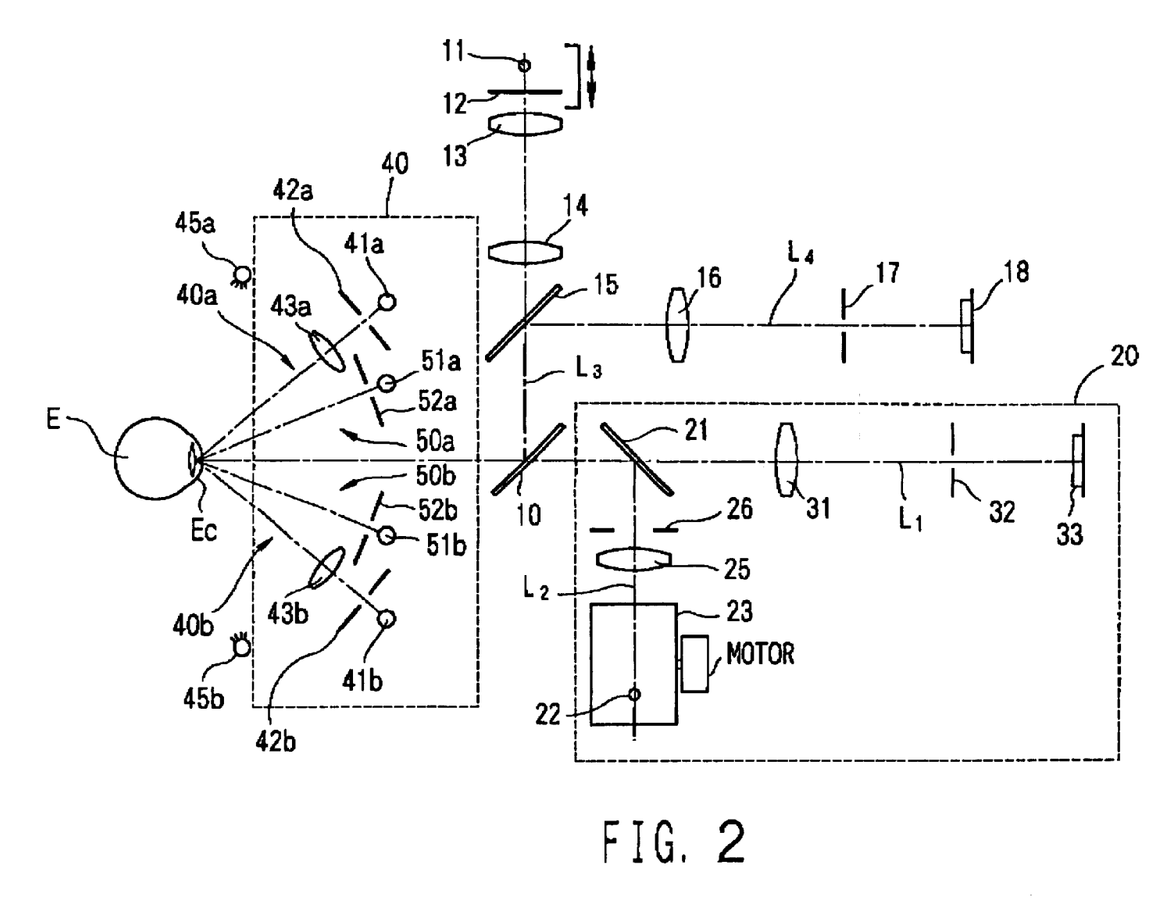
FIG. 2 is a view schematically showing a structure of an optical system included in the ophthalmic apparatus.

A detailed description of one preferred embodiment of a shape measurement apparatus embodied by the present invention is provided below with reference to the accompanying drawings. The description will be given with an example of a handheld-type ophthalmic apparatus capable of measuring eye refractive power and a corneal shape (corneal radius of curvatures). FIG. 1 is an external view schematically showing an ophthalmic apparatus used in the preferred embodiment, and FIG. 2 is a view schematically showing an optical system included in the apparatus.

A measurement window 4 is placed on an examinee's side (a side of an object to be examined) of an apparatus 1, and measurement light from an eye refractive power measurement optical system described later is irradiated (projected) onto an eye E to be examined along a measurement optical axis L1 which goes through the center of the window 4. Besides, an image of an anterior segment of the eye E is picked up via the window 4. Two illumination windows 7a and 7b are provided below the window 4, and illumination light from anterior segment illumination light sources described later illuminates the eye E through each of the windows 7a and 7b.

In addition, four irradiation (projection) windows 8a to 8d are provided vertically and horizontally symmetrical about the window 4 being their center. Target light from a target projection optical system described later is irradiated (projected) onto the eye E through each of the windows 8a to 8d. Right below the windows 8a and 8b are two irradiation (projection) windows 9a and 9b which target light used for detecting alignment condition in a Z-direction (a direction of a working distance) goes through.

A LCD monitor 5 and a switch part 6 are placed on an examiner's side of the apparatus 1. The image of the anterior segment of the eye E, alignment information and measurement information are displayed on the monitor 5. The lower part of the apparatus 1 is a grasping part 2 for the examiner.

In FIG. 2, a half mirror 10 is placed on the optical axis L1 which is a central axis of the apparatus 1 opposed to the eye E, and the eye refractive power measurement optical system 20 is placed on the rear side of the half mirror 10. On the side of an optical axis L2 made coaxial with the optical axis L1 by a half mirror 21, a light source 22 shared for measurement of eye refractive power and detection of alignment condition in X and Y directions (horizontal and vertical directions), a rotation sector 23 having a slit aperture, a projection lens 25, and a limiting diaphragm 26 are placed. The light source 22 emits infrared light. In addition, on the rear side of the half mirror 21 on the optical axis L1, a photo-receiving lens 31, a diaphragm 32, and a photo-receiving part 33 including three pairs of photodetectors are placed. Eye refractive power is measured by obtaining signals indicating the phase difference in accordance with the scanning direction of slit light using the three pairs of photodetectors on the photo-receiving part 33. The measurement of the eye refractive power has little relationship with the present invention, and the details are omitted (see Japanese Patent Application Unexamined Publication Hei10-108836 corresponding to U.S. Pat. No. 5,907,388 for the details).

On an optical axis L3 made coaxial with the optical axis L1 by the half mirror 10, a light source 11 which emits visible light, a fixation target plate 12 on which a fixation target is formed, and lenses 13 and 14 are placed to form a fixation target optical system. The light source 11 and the fixation target plate 12 integrally move in the direction of the optical axis L3 by a fixation target moving part described later to fog the eye E. In addition, a dichroic mirror 15 is placed between the lens 14 and the half mirror 10. On an optical axis L4 on the reflecting side of the dichroic mirror 15 (the optical axis L4 is mode coaxial with the optical axis L3 by the dichroic mirror 15), an image forming lens 16, a telecentric diaphragm 17 and a CCD camera 18 having an image pickup element are placed to form an observation optical system. The CCD camera 18 has a sensitivity of near-infrared and infrared regions. The observation optical system serves as a target detection optical system for detecting targets projected onto the eye E, and as a part of a corneal shape measurement optical system.

Reference numeral 40 indicates the target projection optical system, which is composed of four groups of first target projection optical systems 40a to 40d as a part of the corneal shape measurement optical system placed on the circumference of a single circle having the optical axis L1 at its center, and of second target projection optical systems 50a and 50b for irradiating (projecting) the target light used for detecting the alignment condition in the Z-direction.

The first target projection optical systems 40a and 40b are placed so that each of their projection optical axes intersects with the optical axis L1 at a predetermined angle in the horizontal direction of the apparatus 1. Likewise, the first target projection optical systems 40c and 40d (illustrations are omitted in FIG. 2) are placed so that each of their projection optical axes intersects with the optical axis L1 at a predetermined angle in the vertical direction of the apparatus 1. Reference numeral 41a to 41d are point light sources which emit infrared light, 42a to 42d are spot diaphragms, and 43a to 43d are collimating lenses which project targets at a infinite distance onto the eye E.

The second target projection optical systems 50a and 50b are placed below the first target projection optical systems 40a and 40b (in FIG. 2, 50a and 50b are deviated toward the optical axis L1 for convenience in illustration), and are placed symmetrically with respect to the optical axis L1. The second target projection optical systems 50a and 50b are provided with point light sources 51a and 51b which emit infrared light, and spot diaphragms 52a and 52b, and project targets at a finite distance onto the eye E.

Figure 3:
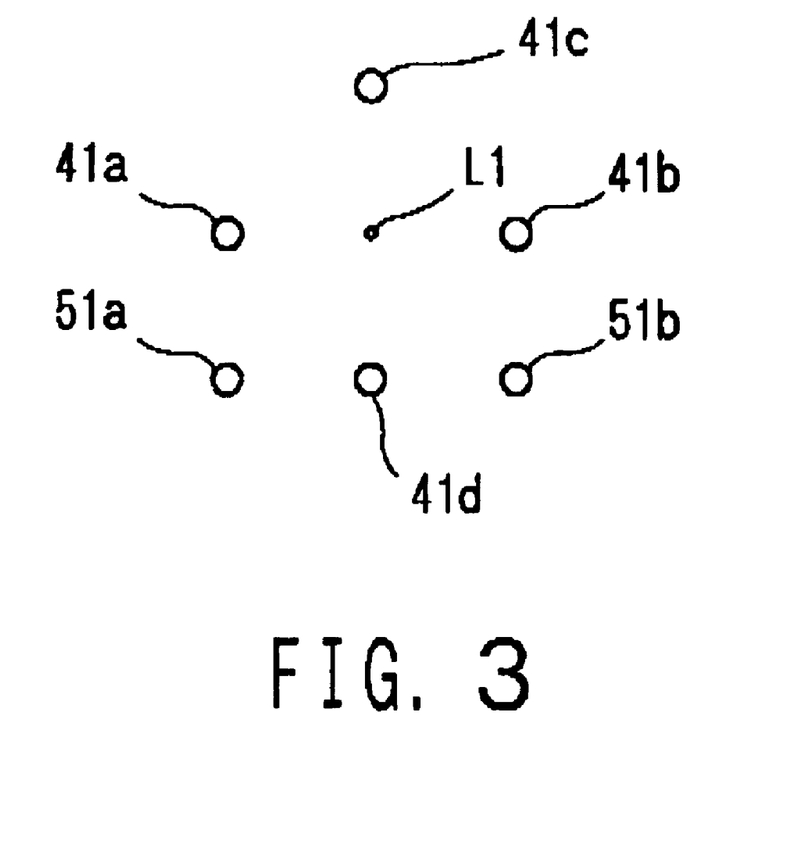
FIG. 3 is a view schematically showing a configuration (arrangement) of each light source when viewed from an examinee's side.

FIG. 3 is a view schematically showing a configuration (arrangement) of the light sources 41a to 41d included in the first target projection optical systems 40a to 40d and the light sources 51a and 51b included in the second target projection optical systems 50a and 50b, when viewed from the examinee's side. The light sources 51a and 51b are placed at positions not symmetrical about a point with respect to the optical axis L1 (an asymmetric pattern). The target projection optical system 40 irradiates light to form totally six reflexes (target images) at the periphery of a cornea Ec of the eye E off the corneal center.

Besides, in FIG. 2, the anterior segment illumination light sources 45a and 45b which emit near-infrared light are placed at the same height as the distance from the optical axis L1, and placed to have a predetermined positional relationship with the optical axis L1, so as to illuminate the eye E from an oblique-lower direction. The light sources 45a and 45b irradiate light at a finite distance, and form two reflexes on the cornea Ec. The reflexes are detected by the camera 18 as target images not symmetric about a point with the optical axis L1 (an asymmetric pattern).

Figure 4:
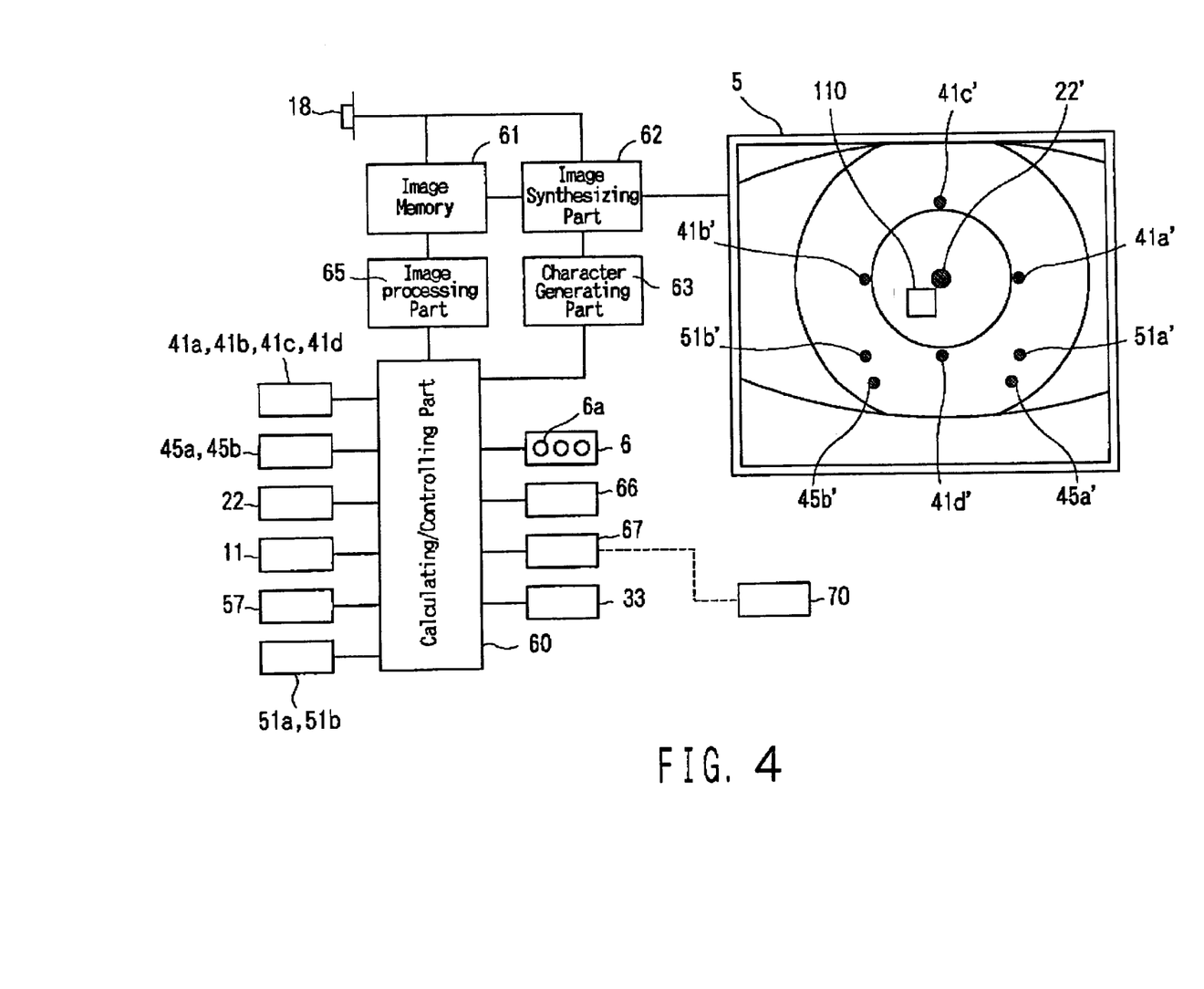
FIG. 4 is a block diagram schematically showing a control system of the ophthalmic apparatus.

FIG. 4 is a block diagram schematically showing, primary parts of a control system of the apparatus 1. An output image from the camera 18 is provided with a predetermined processing and captured in an image memory 61. Besides, the image from the camera 18 is displayed on the monitor 5 via an image synthesizing part 62. A character generating part 63 generates various characters and letters to be displayed on the monitor 5, and a signal therefrom is electrically synthesized with a picture signal from the camera 18 by the image synthesizing part 62. An image processing part 65 detects a signal from the image captured in the image memory 61, and a calculating/controlling part 60 obtains positions of the target images based on the signal detected by the image processing part 65 to measure a spherical shape such as a shape of the cornea Ec, a shape of a contact lens, or the like. In addition, the calculating/controlling part 60 is connected to the light source 22, the light sources 41a to 41d, and the light sources 51a and 51b, the photo-receiving part 33 for measuring the eye refractive power, a fixation target moving part 57 and the like, and controls measurement of the corneal shape and measurement of the eye refractive power and calculates the eye refractive power.

Further, a memory part 66 is capable of storing the obtained spherical shape data (the radius of curvatures and the axial angles of the steepest and flattest meridians) such as the obtained corneal shape data or the like, the obtained eye refractive power data and the like. Various data stored by the memory part 66 are sent to a printer 70 via an outward output part 67 so that measurement data are printed out.

Figure 7:
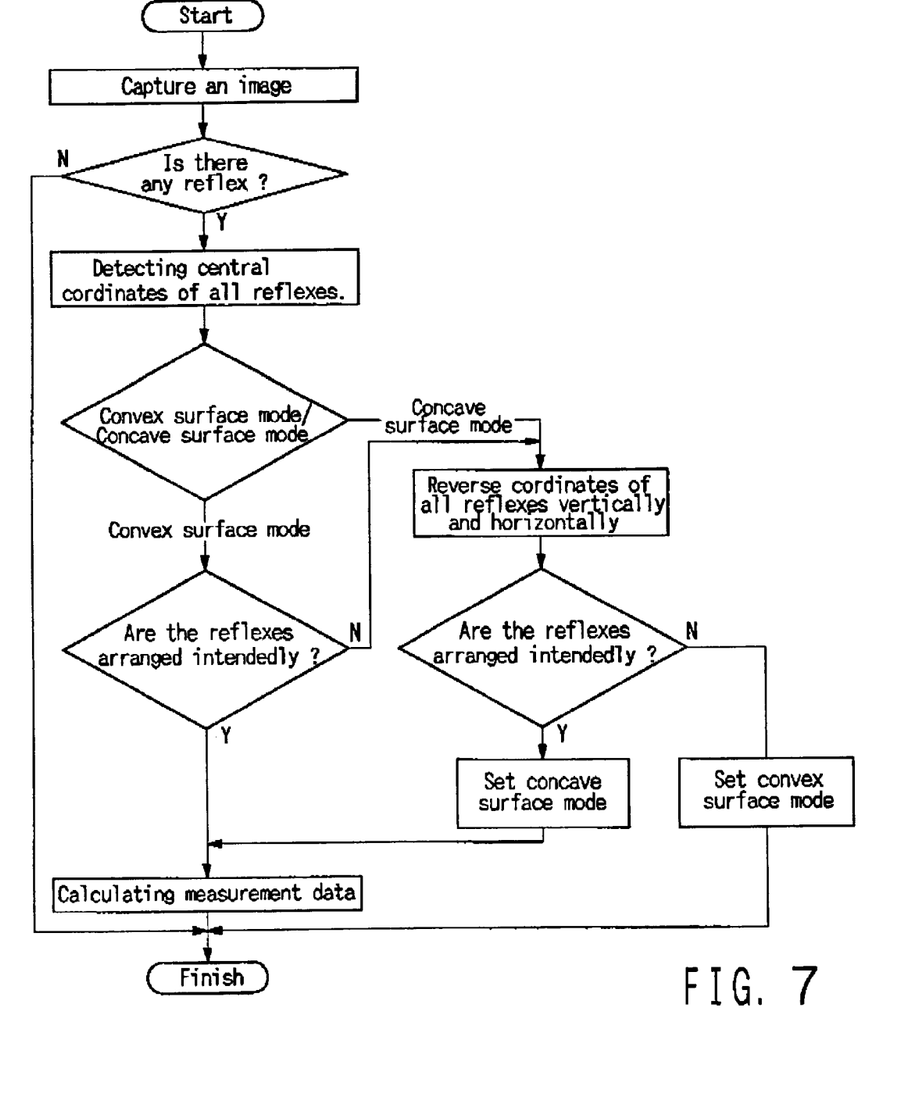
FIG. 7 is a flowchart illustrating a flow of a measurement operation at the time of measurements of a convex surface shape and a concave surface shape.

With the configuration as described above, the operation will be described referring to a flowchart shown in FIG. 7. Firstly, measurement of a spherical shape of a convex surface of the cornea Ec will be described. Secondly, measurement of a spherical shape of a concave surface of a contact lens will be described.

<Measurement of a Spherical (Convex Surface) Shape of a Cornea>

The light source 22, the light sources 45a and 45b, the light sources 41a to 41d, and the light sources 51a and 51b light up, and the window 4 is positioned opposed to the eye E, corneal reflexes of those light sources and an image of the anterior segment are thereby picked up by the camera 18 to be displayed on the monitor 5. On the display of the monitor 5 shown in FIG. 4, reference numerals 22', 41a' to 41d', and 51a' and 51b' indicate the corneal reflexes of the light sources 22, 40a to 40d, and 51a and 51b, respectively. Reference numeral 45a' and 45b' indicate the corneal reflexes of the light sources 45a and 45b. Light emitted from the light source 22 is irradiated (projected) onto the eye E along the optical axis L1 to form the reflex 22' on a corneal vertex.

Further, at a predetermined position on the monitor 5, an aiming marker 110 having a square shape generated by the character generating part 63 is displayed being electrically synthesized by the image synthesizing circuit 62. The center of the aiming marker 110 is considered as an alignment center in X and Y directions, and the examiner performs alignment in the X and Y directions by moving the apparatus 1 with respect to the eye E so that the reflex 22' is positioned at the center of the aiming marker 110. Furthermore, an alignment condition in the Z-direction is detected by comparing the distance between the reflex 41a' and the reflex 41b', with the distance between the reflex 51a' and the reflex 51b' (see Japanese Patent Application Unexamined Publication Hei6-46999 corresponding to U.S. Pat. No. 5,463,430 for judgment of the alignment condition).

From the image of the anterior segment captured in the image memory 61 by the image processing part 65, central coordinates of each reflex (target image) are detected. The control part 60 judges whether the object is measured on the convex surface shape (the measurement of the corneal shape) or on the concave surface shape (the measurement of the base curve of the contact lens), according to the positional relationship among the detected reflexes (a relation in the configuration (arrangement) of the reflexes). Precisely, a configuration (arrangement) pattern of the reflexes at the time of the measurement of the convex surface shape is stored in advance as a reference pattern, then the positional relationship among the reflexes detected by the image processing part 65 is compared with the reference pattern in order to judge whether the measurement is performed on the convex surface or concave surface.

Figure 5:
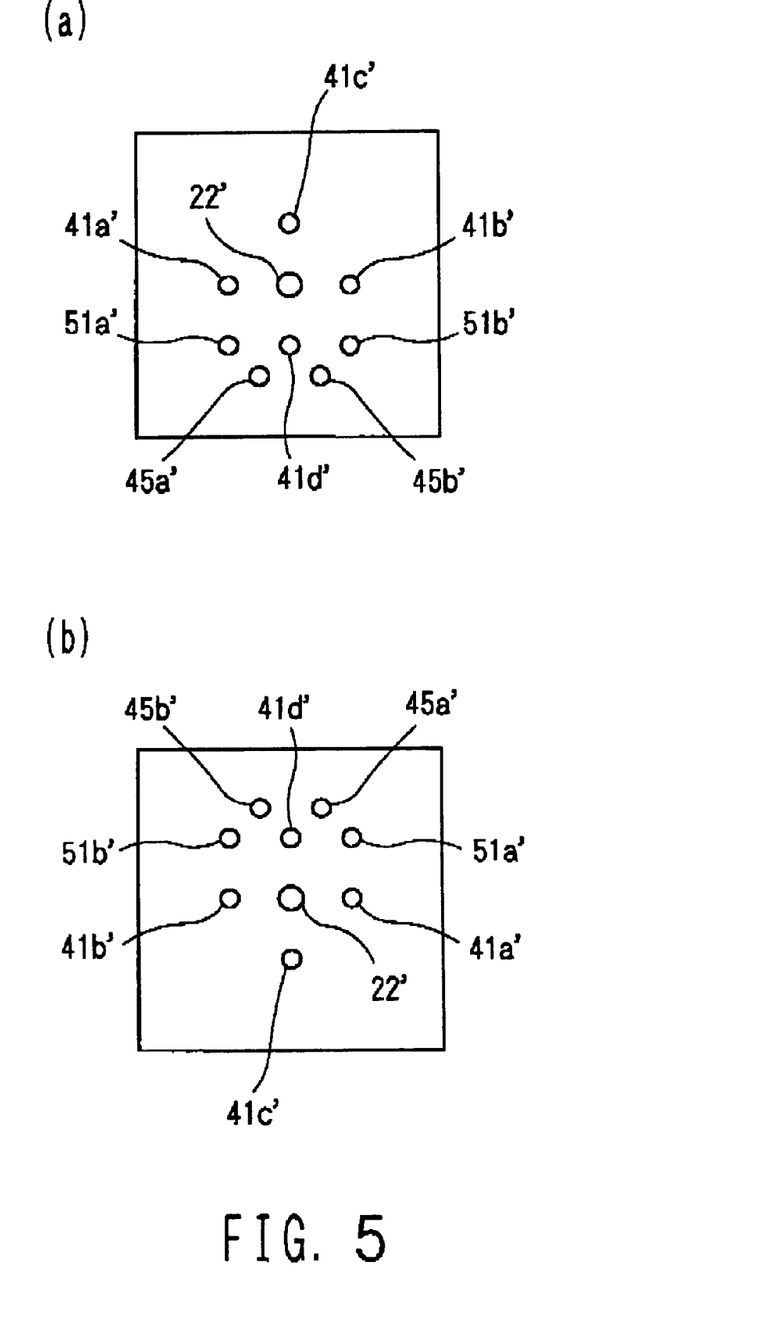
FIGS. 5A and 5B are views schematically showing a positional relationship of each detected reflex (target image)

FIG. 5A is a schematic diagram showing a positional relationship among the reflexes detected at the time of the measurement of the convex surface shape. At the completion of the alignment, the reflex 22' being the central reference point, the reflexes 41a' to 41d', the reflexes 51a' and 51b', and the reflexes 45a' and 45b' are detected in a positional relationship as shown in FIG. 5A. In other words, the reflexes 51a', 51b', 45a' and 45b' are positioned below the reflex 22' being the central reference point. The configuration pattern is stored in the memory part 66 as the reference pattern. When this configuration pattern is detected, the control part 60 judges that the convex surface shape is measured, and controls measurement in the mode for the concave surface shape measurement.

Based on the judgment of the alignment condition in the Z-direction and in the X and Y directions, the control part 60 starts the measurement automatically giving a trigger signal when the predetermined alignment condition is completed. The control part 60 calculates the corneal shape data of the eye E such as the corneal radius of curvatures, the axial angle and the like, based on a photo-received position (a detected position) of the reflexes 41a' to 41d' detected by the image processing part 65. The calculated corneal shape data are stored into the memory part 66 while being displayed on the monitor 5 by the character generating part 63. At the time of the corneal shape measurement, the corneal radius of curvatures and the axial angle may be calculated if three reflexes (target images) are detected as described in Japanese Patent No. Hei1-19896.

The corneal shape data are sent to the printer 70 via the outward output part 67 using the print switch provided in the switch part 6 in order to be printed out. At this time, the data may be clearable if provided with a notice informing whether the convex surface shape measurement or the corneal shape measurement.

<Measurement of a Spherical (Concave Surface) Shape of a Contact Lens>

Figure 8:
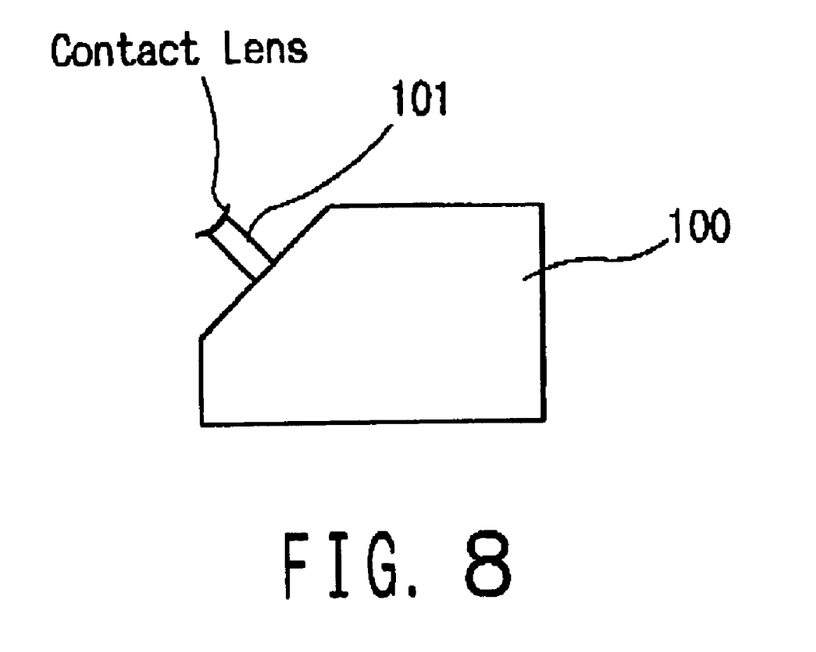
FIG. 8 is a view schematically showing a fixed jig holding a contact lens.

Next, the measurement of the base curve of the contact lens will be described. After pouring water into a concave part formed on a holder 101 of a fixed jig 100 shown in FIG. 8, the convex surface of the contact lens is mounted on the holder 101. Then, the same alignment as that for the measurement of the corneal shape is performed on the concave surface of the contact lens, and an automatic measurement is performed. At this point, the control part 60, as described above, detects the positional relationship among the reflexes (target images) detected by the image processing part 65 from the image of the anterior segment captured in the image memory 61 by the camera 18, and judges whether the object is measured on the convex surface shape (the measurement of the corneal shape) or the concave surface shape (the measurement of the base curve of the contact lens).

FIG. 5B is a schematic diagram showing a positional relationship among the reflexes detected at the time of the measurement of the concave surface shape. In measuring the concave surface shape, a configuration (arrangement) pattern of the reflexes is obtained by vertically and horizontally reversing that obtained at the time of the measurement of the convex surface shape shown in FIG. 5A with respect to the reflex 22'. That is, the reflexes 51a', 51b', 45a' and 45b' are positioned above the reflex 22'. When the reflexes are detected with such a configuration pattern, that pattern does not coincide with the reference pattern. Therefore, the coordinates of all of the detected reflexes are reversed vertically and horizontally (rotated 180 degrees about the measurement optical axis on the image). Then, the configuration pattern becomes applied to the condition of the reference pattern. If the configuration pattern after the calculation coincides with the condition of the reference pattern, the control part 60 confirms that the analysis common to the measurement of the concave surface shape can be performed, and sets the mode for the concave surface shape measurement.

Further, when the concave surface shape of the contact lens is judged to be under measurement, the control part 60 displays letters "CL" on the monitor 5 using the character generating part 63 to inform the examiner of the measurement of the base curve of the contact lens.

Furthermore, in order to suppress reflection light (a back-surface reflection) from the convex surface of the contact lens, the control part 60 makes adjustments so that target projection light intensity of each light source is reduced within a range where the radius of curvatures may be calculated while the back-surface reflection is suppressed (the reduction of the light intensity may be applied to light sources used at least for the spherical shape measurement.) Detecting sensitivity to the reflexes may be reduced instead. This reduction may be performed by adjusting photo-receiving sensitivity of the camera 18, using the circuit of the image processing part 65 or a processing software thereof, and the like.

As in the case of the measurement of the corneal shape, when the predetermined alignment condition is completed, the control part 60 starts the measurement automatically giving the trigger signal, calculates the radius of curvatures and the axial angle of the concave surface of the contact lens, and displays the calculated result on the monitor 5. At this time, if the contact lens to be measured is for astigmatic correction, it is necessary to calculate the axial angle. For this purpose, the control part 60 performs calculation for horizontally reversing a principal meridian axial angle (AXIS) obtained from the four reflexes for the spherical shape measurement (i.e. transform the axial angle of 45 to 135 degrees), and displays a value applied to the axial angle in the case of wearing contact lens (the axial angle when viewed from the convex surface) as the measurement result. In addition, at the same time, the control part 60 makes the memory part 66 store the obtained shape data (the radius of curvatures and the axial angle on the concave surface) as the data from the measurement of the base curve of the contact lens. The shape data stored into the memory 66 is sent to the printer 70 via the outward output part 67 using the print switch provided in the switch part 6, and printed out with the letters "CL" indicating that the shape data is obtained from the measurement of the base curve of the contact lens.

Besides, the measurement mode in the initial state of the apparatus 1 is set for the convex surface shape, which is for the corneal shape measurement. After setting the mode for the concave surface shape measurement, the mode is kept the same till it is changed to the mode for the convex surface shape measurement. Once the mode is changed for the concave surface shape measurement, if the coordinates of all the reflexes are reversed vertically and horizontally, and a judgment is made whether or not they comply with the condition of the reference pattern, the calculation may be performed effectively. And, when the convex surface shape is measured again, since the configuration pattern of the reflexes is not compatible with the condition of the reference pattern, the configuration pattern is reversed vertically and horizontally again. If the reversed configuration pattern coincides with the condition of the reference pattern, it is judged that the convex surface shape measurement has been performed. Then, the vertical and horizontal reverse may be stopped.

The vertical and horizontal reverse of the reflexes requires a simple calculation and a short processing time. Therefore, if the configuration pattern of the reflexes is judged not compatible with the condition of the reference pattern, the reflexes may be reversed vertically and horizontally so as to be judged with respect to the condition of the reference pattern again. In addition, in the preferred embodiment, when the concave surface shape is measured, the reflexes are reversed vertically and horizontally, and the same calculation as that for the convex surface shape measurement is performed thereon to obtain measurement data. However, the present invention is not limited thereto. When the reflexes are not arranged intendedly, another program different from that program for the convex surface shape measurement may be run for the concave surface shape measurement to calculate the measurement data.

Further, the mode for the convex surface shape measurement and that for the concave surface shape measurement are not set automatically, but may be set by manual operation by the examiner using a mode changing switch 6a placed in the switch part 6.

Furthermore, the mode for the concave surface shape measurement may be that for the contact lens as well. Generally, in measuring a contact lens using this kind of ophthalmic apparatus, a concave surface shape is measured to obtain the base curve data. When the measurement mode is selected for the contact lens, the control part 60 displays the letters "CL" on the monitor 5 and on the printed-out data, and sets the measurement condition such as reducing the light intensity of the measurement light for the spherical shape measurement.

Figure 6:
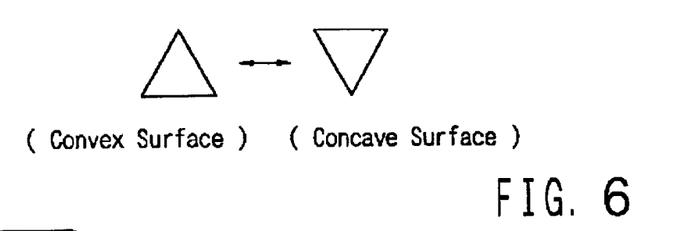
FIG. 6 is a view schematically showing a modification of a pattern of a target.

In the preferred embodiment described above, totally nine reflexes are provided on the eye E, including the illumination light, but the present invention is not limited thereto. For example, the reflexes of a number which is capable of performing the measurement of the corneal shape and the like, may be formed on the object, while the targets projected onto the object may be arranged in an asymmetric pattern with respect to the optical axis L1. Since the corneal radius of curvatures may be measured by projecting two targets being symmetrical about a point and one target on the circumference of the same circle as the two targets, the targets for judging whether the convex or concave surface may be used as the measurement targets. Moreover, it is essential only that the targets for judging whether the convex or concave surface have an asymmetric pattern. For example, a triangle-shaped pattern as shown in FIG. 6 may be used.

Furthermore, in the preferred embodiment, the reference pattern stored in advance and the configuration pattern of the actual reflexes are consistent with each other, but the present invention is not limited thereto. For example, among the plural reflexes detected by the camera 18, the detecting condition of part of the reflexes are captured to detect whether the convex or concave surface is measured. When using the nine reflexes presented in the preferred embodiment, as shown in FIG. 5A, if one of the reflexes at the upper edge of the image of the anterior segment and two of the reflexes at the lower edge are detected, it may be judged that the convex surface shape is measured.

As above, in the preferred embodiment, the description is given to the handheld-type ophthalmic apparatus provided with functions of the corneal shape measurement and the eye refractive power measurement. However, the present invention is not limited thereto. For example, the present invention may be applied to an ophthalmic apparatus of a stationary type or an apparatus having only the function of the corneal shape measurement. Additionally, the present invention may simply be applied to an apparatus for measuring a spherical shape of the convex and concave surfaces of correctives like the contact lens, the spectacles lens and the like. In this case, it is judged whether the measurement is on the convex or concave surface, and the judgment result is therefore added to the measurement data to be displayed and printed out, thereby eliminating the trouble of management by the examiner.

As described above, according to the present invention, the apparatus may be provided, which is capable of avoiding troubles for the examiner and has an excellent operability. In addition, the measurement accuracy is improved.

The foregoing description of the preferred embodiments of the invention has been presented for purposes of illustration and description. It is not intended to be exhaustive or to limit the invention to the precise form disclosed, and modifications and variations are possible in the light of the teachings described above or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A shape measurement apparatus for measuring a spherical shape of an object to be examined, the apparatus comprising:
   a measurement unit including:
      a first projection optical system which projects first targets for measurement onto a spherical surface to be measured of an object to be examined;
      a first detection optical system which detects images of the projected first targets; and
      a calculation unit which obtains a shape of the spherical surface based on the detected images of the first targets;
   an output unit which outputs the obtained shape of the spherical surface;
   a mode setting unit which sets any one of a first measurement mode for measuring a convex shape and a second measurement mode for measuring a concave shape; and
   a condition setting unit which sets at least one of a measurement condition and an output condition based on a mode setting result, the measurement condition and the output condition in the first measurement mode being different from the measurement condition and the output condition in the second measurement mode.

2. The shape measurement apparatus according to claim 1, wherein the measurement condition includes at least one of projection light intensity of the first targets and detecting sensitivity of the first detection optical system.

3. The shape measurement apparatus according to claim 1, wherein the output condition includes horizontally or laterally reversing a principal meridian axial angle of the obtained spherical surface to output when the second measurement mode is set.

4. The shape measurement apparatus according to claim 1, further comprising:
   a second projection optical system which projects second targets of a configuration or shape pattern not symmetric about a point with respect to a measurement reference axis onto the spherical surface;
   a second detection optical system which detects images of the projected second targets; and
   a judging unit which judges whether the spherical surface is the convex shape or the concave shape based on a pattern of the detected images of the second targets;
   wherein the mode setting unit sets any one of the first measurement mode and the second measurement mode based on a judgment result.

5. The shape measurement apparatus according to claim 4, wherein the judging unit includes a memory which stores a reference pattern for the convex or concave, and judges whether the spherical surface is the convex shape or the concave shape based on a comparison between the pattern of the detected images of the second targets and the stored reference pattern.

6. The shape measurement apparatus according to claim 4, wherein the second projection optical system projects at least either the second targets for detecting a working distance or the second targets for illuminating an anterior segment of an eye.

7. A shape measurement apparatus according to claim 4, wherein the first projection optical system doubles as the second projection optical system, and projects at least part of the first targets as the second targets.

8. A shape measurement apparatus for measuring a spherical shape of an object to be examined, the apparatus comprising:
   a measurement unit including:
      a first projection optical system which projects first targets for measurement onto a spherical surface to be measured of an object to be examined;
      a first detection optical system which detects images of the projected first targets; and
      a calculation unit which obtains a shape of the spherical surface based on the detected images of the first targets;
   a second projection optical system which projects second targets of a configuration or shape pattern not symmetric about a point with respect to a measurement reference axis onto the spherical surface;
   a second detection optical system which detects images of the projected second targets; and
   a judging unit which judges whether the spherical surface is a convex shape or a concave shape based on a pattern of the detected images of the second targets.

9. The shape measurement apparatus according to claim 8, wherein the judging unit includes a memory which stores a reference pattern for the convex or concave, and judges whether the spherical surface is the convex shape or the concave shape based on a comparison between the pattern of the detected images of the second targets and the stored reference pattern.

10. The shape measurement apparatus according to claim 8, the second projection optical system projects at least either the second targets for detecting a working distance or the second targets for illuminating an anterior segment of an eye.

11. The shape measurement apparatus according to claim 8, wherein the first projection optical system doubles as the second projection optical system, and projects at least part of the first targets as the second targets.

12. The shape measurement apparatus according to claim 8, further comprising a mode setting unit which sets any one of a first measurement mode for measuring the convex shape and a second measurement mode for measuring the concave shape, based on a judgment result.

* * * * *